United States Patent
Krebs et al.

(10) Patent No.: US 10,653,783 B2
(45) Date of Patent: May 19, 2020

(54) SUSTAINED RELEASE OF BIOACTIVE FACTORS FROM ZWITTERIONIC HYDROGELS

(71) Applicant: Colorado School of Mines, Golden, CO (US)

(72) Inventors: Melissa D. Krebs, Englewood, CO (US); Gulsu Sener Yildirim, Boulder, CO (US)

(*) Notice: Subject to any disclaimer, the term of this patent is extended or adjusted under 35 U.S.C. 154(b) by 0 days.

(21) Appl. No.: 15/808,374

(22) Filed: Nov. 9, 2017

(65) Prior Publication Data
US 2018/0221490 A1 Aug. 9, 2018

Related U.S. Application Data

(60) Provisional application No. 62/419,742, filed on Nov. 9, 2016.

(51) Int. Cl.
| | |
|---|---|
| *A61K 47/32* | (2006.01) |
| *C08F 120/38* | (2006.01) |
| *C08J 9/00* | (2006.01) |
| *A61K 9/06* | (2006.01) |
| *A61K 38/16* | (2006.01) |
| *C08F 220/38* | (2006.01) |

(52) U.S. Cl.
CPC ............... *A61K 47/32* (2013.01); *A61K 9/06* (2013.01); *A61K 38/16* (2013.01); *C08F 120/38* (2013.01); *C08F 220/38* (2013.01); *C08J 9/0061* (2013.01); *C08J 2201/026* (2013.01); *C08J 2205/022* (2013.01); *C08J 2205/044* (2013.01); *C08J 2205/05* (2013.01); *C08J 2207/10* (2013.01); *C08J 2333/14* (2013.01)

(58) Field of Classification Search
CPC .......... A61K 38/16; A61K 47/32; A61K 9/06; C08F 120/38; C08J 2205/022; C08J 2205/044; C08J 2207/10; C08J 2333/14; C08J 9/0061
See application file for complete search history.

(56) References Cited

U.S. PATENT DOCUMENTS

| | | | | |
|---|---|---|---|---|
| 5,981,826 A | * | 11/1999 | Ku | A61L 27/38 602/49 |
| 2014/0227327 A1 | * | 8/2014 | Bencherif | A61K 9/7007 424/400 |
| 2015/0166696 A1 | * | 6/2015 | Plotkin | A61K 9/146 428/402 |
| 2015/0299415 A1 | * | 10/2015 | Kennedy | C08J 9/28 424/400 |

OTHER PUBLICATIONS

Ajmal et al. (Colloids and Surfaces A: Eng. Aspects 486 (2015) 29-37) (Year: 2015).*
Newland et al. (small 2015, 11, No. 5047-5053) (Year: 2015).*
Chen, Pen-Chung et al., "Injectable microparticle—gel system for prolonged and localized lidocaine release. II. In vivo anesthetic effects", Wiley Periodicals, Inc., Jul. 1, 2004, pp. 459-466.
Lin, Chien-Chi et al., "PEG Hydrogels for the Controlled Release of Biomolecules in Regenerative Medicine", Pharmaceutical Research, vol. 26, No. 3, Dec. 18, 2008, pp. 631-643.
Newland, Ben et al., "Tackling Cell Transplantation Anoikis: An Injectable, Shape Memory Cryogel Microcarrier Platform Material for Stem Cell and Neuronal Cell Growth", Small vol. 11 No. 38, Aug. 3, 2015, pp. 5047-5053.
Pakulska, Malgosia M. et al., "Hybrid Crosslinked Methylcellulose Hydrogel: A Predictable and Tunable Platform for Local Drug Delivery", Adv. Mater. 27, 2015, pp. 5002-5008.
Percin, Isik et al., "Comparison of Two Different Reactive Dye Immobilized Poly(Hydroxyethyl Methacrylate) Cryogel Discs for Purification of Lysozyme", Springer; Appl Biochem Biotechnol No. 175, Jan. 6, 2015, pp. 2795-2805.
Tamahkar, Emel et al., "Molecularly imprinted supermacroporous cryogels for cytochrome c recognition", J. Sep. Sci. 34, Sep. 9, 2011, pp. 3433-3440.
Welzel, Petra B. et al., "Cryogel Micromechanics Unraveled by Atomic Force Microscopy-Based Nanoindentation", Adv. Healthcare Mater. 3, 2014, pp. 1849-1853.
Derazshamshir, Ali et al., "Molecularly Imprinted PHEMA-Based Cryogel for Depletion of Hemoglobin from Human Blood", Macromol. Chem. Phys. vol. 211, 2010, pp. 657-668.
Lozinsky, Vladimir I. et al., "Polymeric cryogels as promising materials of biotechnological interest", TRENDS in Biotechnology; vol. 21 No. 10, Oct. 2003, pp. 445-451.
Savina, Irina N. et al., "Cryogels from poly(2-hydroxyethyl methacrylate): macroporous, interconnected materials with potential as cell scaffolds", Soft Matter, vol. 3, Jun. 15, 2007, pp. 1176-1184.
Wu, Yuzhou et al., "Programmable protein—DNA hybrid hydrogels for the immobilization and release of functional proteins†", Chem. Commun., vol. 50, Sep. 10, 2014, pp. 14620-14622.
Yan, Ming et al., "A novel intracellular protein delivery platform based on single-protein nanocapsules", Nature Nanotechnology vol. 5, Jan. 2010, pp. 48-53.
Zhang, Lei et al., "Zwitterionic hydrogels implanted in mice resist the foreign-body reaction", Nature Biotechnology vol. 31 No. 6, Jun. 2013, pp. 553-557.

* cited by examiner

*Primary Examiner* — Anna R Falkowitz
(74) *Attorney, Agent, or Firm* — Dorsey & Whitney LLP (57) ABSTRACT

Methods of producing microporous zwitterionic cryogels are described, wherein the cryogels are useful for sustaining release of therapeutic agents. The disclosed cryogels overcome several limitations associated with existing compositions, for example the disclosed cryogels have high loading efficiencies and a sustained release profile with minimal burst of up to 4 months or more. The characteristics of the disclosed cryogels can be varied by altering monomer (e.g. zwitterion) and crosslinker selection. The amount of monomer contained in the hydrogel may also be varied to aid in controlling the cryogel's chemistry.

19 Claims, 6 Drawing Sheets

Fig. 8

SUSTAINED RELEASE OF BIOACTIVE FACTORS FROM ZWITTERIONIC HYDROGELS

CROSS-REFERENCE TO RELATED APPLICATIONS

This application claims benefit of priority pursuant to 35 U.S.C. § 119(e) of U.S. provisional patent application No. 62/419,742 entitled "SUSTAINED RELEASE OF BIOACTIVE FACTORS FROM ZWITTERIONIC HYDROGELS," filed on Nov. 9, 2016, which is hereby incorporated by reference in its entirety.

FIELD

This work is directed to processes, methods, and compositions for the sustained release of therapeutic agents from zwitterionic polymeric hydrogels, especially cryogels.

BACKGROUND

Hydrogels have been considered as promising materials for controlled delivery of macromolecular therapeutics such as proteins, peptides, and genes, due to their good biocompatibility and tunable mechanical and chemical properties. However, the high water content of hydrogels generally results in a rapid release of macromolecular therapeutics (typically a few hours) with a large burst release. Burst release of therapeutics not only decreases the efficiency of the therapy but also can cause serious side effects due to the sudden increase of drug concentration in the blood. In addition, efficient loading of macromolecular therapeutics to the hydrogels is challenging. While adding therapeutics into the hydrogel preparation solution is straightforward, this method generally results in low loading yield due to release of therapeutics during hydrogel cleaning (washing) steps. Also, some hydrogel preparation methods, including heating and/or sonication, can denature or degrade these biomolecules. Alternatively, macromolecular therapeutics can be loaded to the hydrogels after synthesis by passive diffusion of the proteins into the polymer network. However, rapid release of proteins with a large burst release is often observed for this approach. To overcome these limitations, recently, several other strategies such as photo-crosslinking, physical crosslinking, and addition of drug-laden microparticles have been reported; however, in only a few of these studies were good loading yield and sustained and burst-free release profiles achieved. Therefore, development of alternative hydrogel formulations to address the aforementioned limitations in hydrogel-based macromolecular therapeutic delivery platforms is still needed.

SUMMARY

Disclosed herein are compositions and methods to produce microporous zwitterionic cryogels for the sustained release of therapeutic agents. The disclosed compositions may overcome several limitations associated with the application of hydrogels for sustained drug delivery. For example, in some embodiments the disclosed cryogel demonstrates high loading efficiencies of a therapeutic agent, combined with a sustained release profile while minimizing burst release. The disclosed cryogels can be formulated with different monomers and crosslinkers to vary their chemistry. The amount of monomer contained in the hydrogel may also be varied to aid in controlling the cryogel's chemistry. For example, in some embodiments the protein loading efficiency was varied from 38% to 72% by increasing the concentration of the zwitterionic monomer. In one embodiment, a sustained release of therapeutic agent lasted 4 months.

DETAILED DESCRIPTION

Disclosed herein are compositions and methods to produce hydrogels for the sustained release of therapeutic agents. The disclosed hydrogel compositions may be used for the prevention and/or treatment of certain diseases that may benefit from local and sustained drug delivery. The disclosed compositions may overcome several limitations associated with the current application of hydrogels for sustained drug delivery. For example, in some embodiments the hydrogel may promote a high protein loading efficiency and may also exhibit a sustained release with very little to no burst release. The disclosed hydrogels can be created from various monomers and crosslinkers, and the concentrations of monomer and crosslinker can be adjusted to vary the hydrogel's loading and release characteristics. In one embodiment the protein loading efficiency was varied from 38% to 72% by increasing the concentration of the monomer in cryogel.

Disclosed herein are methods of creating a zwitterionic hydrogel having interconnected pores of about 50-100 μm. In most embodiments, the disclosed zwitterionic gel is a cryogel formed under cryogelation conditions. In many embodiments, the disclosed cryogel has a denser polymer network than a gel formed under non-cryogelation conditions.

Applications

The disclosed hydrogels are useful in many different applications. These highly biocompatible materials can be used in any clinical application, for example applications where a sustained release of protein drugs or other therapeutic agents to a specific site of the body or tissue is desirable. In some embodiments the hydrogel may be formulated into a removable, permanent, or biodegradable implant. While in other embodiments the hydrogel may be used to create a coating on an implant, or to coat an internal surface of a case or container, for example a case or container for housing a removable implant. Other applications may be non-medical.

Diseases, Conditions, and Indications

The disclosed hydrogels may be useful in treating subjects by delivering a therapeutic compound to various tissues. The disclosed hydrogel may be delivered topically or subcutaneously, and may be formed into various shapes and/or devices. For example, the hydrogel may be formed into a patch or lens for applying to various structures, such as the surface of an eyeball. In some embodiments, the disclosed hydrogels may be used to prevent and/or treat symptoms of certain ophthalmic disorders such as infections, inflammation, allergy conjunctivitis, dry eye, and glaucoma. These conditions are usually treated with a topical therapeutic agent in the form of drops or ointments. In many embodiments, the therapeutic agent in ophthalmic drops and ointments may be combined with the disclosed hydrogel and applied to the surface of an eyeball. In some embodiments, the therapeutic agent may be combined with a hydrogel forming all or part of a contact lens that can then be applied to the surface of the eyeball to provide sustained release of the therapeutic agent. These therapeutic contact lenses may also be used to protect and promote healing of a compromised, damaged, or diseased ocular surface that may be the result of trauma, surgery, corneal dystrophy, persistent epithelial defect, or the like. In yet another embodiment, the hydrogel may be used to coat the inside surface of a container that may be prone to microbial contamination, for example the inside surface of a contact lens case. In this embodiment, the hydrogel coating may be used to release a therapeutic agent into the contact lens solution and help prevent microbial contamination of the lens case.

The disclosed hydrogels may be placed subcutaneously to deliver a therapeutic agent beneath the tissue and/or skin. In some embodiments, the disclosed hydrogels may be used to deliver therapeutic peptides, proteins, and small molecules subcutaneously. For example, the disclosed hydrogels can be placed in the surgical bed after removal of tumors to prevent recurrence of cancer by slowly releasing chemotherapy or immunotherapy agents. The effectiveness of this treatment may be improved by use of a biodegradable hydrogel. The use of such compositions and methods may result in an improved patient response, may reduce the cost of treatment, and/or lessen unwanted side effects that can occur in systemic intravenous delivery methods, especially for treatment sites that are difficult to access.

In some embodiments, hydrogel implants may provide for the sustained delivery of therapeutic hormones. Hormone or endocrine therapy is used to treat or alleviate a wide variety of symptoms including migraines, acne, weight gain, joint and muscular pain, fatigue, insomnia, anxiety, depression, hot flashes, memory loss, sexual problems, vaginal dryness, incontinence, etc. Hormone therapy may also be used to prevent or slow down the loss of bone density, slow or stop the growth of certain tumors, and alleviate the symptoms from endometrious, uterine fibroids, menopause or andropause, central precocious puberty, and to prevent pregnancy. In many embodiments, a hydrogel implant may be placed under the skin of the patient, at or near, for example, the upper arm, lower abdomen, or upper buttocks. This subcutaneous application of the hydrogel may aid in releasing physiologic levels of the therapeutic hormone over an extended period of time. In some embodiments, the hydrogel implant may be removed after a prescribed period of time, or the hydrogel may dissolve over time and be absorbed or removed by the body.

The disclosed hydrogel implants or hydrogel coated implants may also be formulated for the sustained release of antiviral or microbicides via gels and vaginal rings or diaphragms. Microbicides are compounds that can prevent the spread of sexually transmitted infections such as hepatitis B and human immunodeficiency virus (HIV). Worldwide there are approximately 39.4 million cases of HIV infection. In more developed countries, patients may have better access to oral anti-retroviral drugs to reduce the amount of virus in an infected patient and to barrier contraception method that protect against the spread of HIV. In developing nations, however, there is the need for affordable and accessible methods that provide sustained protection. In some embodiments it may be beneficial to combine the release of microbicides with the simultaneous release of progesterone for contraception.

Hydrogels

The disclosed hydrogels are three-dimensional networks of polymer chains that may be crosslinked by physical and/or chemical methods. The disclosed hydrogels can be a solid or semi-solid, scaffold, gel, film, or coating comprised of natural and/or synthetic polymers. In many embodiments the polymer may be a hydrophobic or hydrophilic polymer. Hydrogels may be absorbent and may possess excellent antifouling properties and biocompatibility. In some cases, biocompatibility may be due to the hydrogel's high water content and physiochemical similarity to native extracellular networks. The disclosed polymer network may be formed from a single monomer or combinations of monomers. The polymers of the disclosed hydrogel may be comprised of monomers that have two or more charged groups over a given pH range. In most embodiments the polymers may be comprised of zwitterionic monomers. Crosslinking may be achieved by ionic-, covalent-, photo-crosslinking or combinations thereof. In many embodiments, various characteristics (e.g., loading, elasticity, porosity, degradation rate, viscosity, antifouling properties, etc.) of the hydrogel may be modified by varying the concentration of monomer subunits and density of the crosslinking.

As used herein, a zwitterionic monomer is any compound that is able to be polymerized, wherein the monomer may simultaneously include both a positively and negatively charged group under physiological conditions. The zwitterionic polymers for use in the disclosed hydrogels may include: [2-(methylacryloyloxy)ethyl]dimethyl-(3-sulfoproplyl)ammonium hydroxide (SBMA), sulfobetanine acrylamide, methacryloyloxyethyl phosphorylcholine, carboxybetaine acrylamide and carboxybetaine methacrylate, and combinations thereof. In many embodiments the zwitterionic polymer is SBMA. In some embodiments the disclosed zwitterionic hydrogels may be biodegradable. For example, the hydrogels may be made to be redox responsive by using disulfide bridged crosslinkers (e.g., bis(acryloyl)cystamine) and they can be degraded by incorporation of matrix metalloproteinases (MMP) sensitive peptide sequences into the backbone of the crosslinker. In some embodiments the hydrogel may be crosslinked by adding a crosslinking compound or agent. Exemplary crosslinking agents include: glycerol dimethyacrylate (GDMA), N,N'-methylbis(acrylamide) (MBA), poly(ethylene glycol) diacrylates or methacrylates, ethylene glycoldimethacrylate (EGDMA) and combinations thereof. In most embodiments, initiator compound(s) may be used to start the polymerization process, for example ammonium persulfate (APS) and N,N,N',N'-tetramethylethylene diamine (TEMED).

The disclosed hydrogels may possess a macroporous structure, with interconnected pores. There are multiple methods known in the art to create an interconnected macroporous structure, including inducing phase separation in the gel solution, using sacrificial particles, or using cryogelation conditions. In most embodiments, the disclosed zwitterionic gels are formed under cryogelation conditions and the resulting gel may be referred to as a cryogel or cryotopic gel. Cryogelation refers to gelation under conditions where the temperature is below the freezing point of the aqueous phase of the gel solution. The disclosed cryogel may be synthesized in semi-frozen liquid media in which ice crystals forming in the media act as porogen (pore generator) to create interconnected macro-pores after thawing. The shape and size of the ice crystals may help to modify the morphology and the porosity of the resulting cryogel. The cryogelation temperature may be any temperature below the freezing point of the aqueous phase of the gel solution. Factors such as ratio of polymer subunits, density of the crosslinks in the network, cryogelation temperature, rate of freezing, and solvent composition may be used to modify the characteristics of the cryogel, for example the pore size and density. In most embodiments, the average pore size of the disclosed cryogels may be between about 50 µm and about 100 µm.

Therapeutic Agents

Therapeutic agents for use with the disclosed hydrogels may be various compounds administered to a mammal for a therapeutic purpose such as preventing, treating, reversing, alleviating, inhibiting, or ameliorating a disease or at least one clinical symptom of a disease. The disclosed therapeutic agent may be a biological compound or bioactive factor. In many embodiments, the therapeutic agent is selected from pharmaceutical compounds, molecules, proteins, peptides, nucleic acids, genes, and combinations thereof. Proteins include hormones, peptides, antibodies and antibody fragments. In some embodiments, the disclosed antibody may comprise one or more polypeptides encoding all or part of the immunoglobulin genes, for example one or more variable regions. As used herein, a therapeutic agent may be naturally or synthetically derived. Covalent modifications to the disclosed therapeutic agent are included within the scope of the therapeutic agents disclosed herein and can include the addition of a labeling group such as, but not limited to, isotopic labels, magnetic labels, redox additives, optical dyes, biotinylated groups, and predetermined polypeptide epitopes recognized by a secondary reporter. The disclosed therapeutic agents may also include a prodrug, which may metabolize into a pharmacological active drug after administration.

Some exemplary therapeutic agents for use with the disclosed hydrogels are provided herein, while others are well known to the skilled artisan. The disclosed hydrogels, while not limited to the following agents or uses, may be formulated to deliver one or more of: therapeutic hormones such as progesterone for contraception or other therapeutic purposes, estradiol and/or testosterone for the relief of menopausal and andropausal symptoms or for other therapeutic purposes, histrelin acetate for the treatment of central precocious puberty, and goserelin and leuprolide for the treatment of certain cancers; protein drugs such as Interleukins or anti vascular endothelial growth factor (anti-VEGF) for the immunotherapy of certain cancers; antiviral medications such as tenofovir, dapinvirine, and acyclovir for the treatment and/or prevention of HIV and hepatitis B; antifungal medications such as econazole for the treatment of eye infections; antibiotics such as tobramycin for the treatment of bacterial conjunctivitis; antihistamines such as ketotifen for the treatment of allergy conjunctivitis; anti-inflammatory agents such as dexamethasone for the treatment of ocular inflammation; immosuppresive agents cyclosporin A for the treatment of dry eyes; and beta-blockers such as latanoprost for the treatment of glaucoma.

Loading of Therapeutic Agents

The disclosed hydrogels may be loaded with a therapeutic agent. Loading of a therapeutic agent may be active or passive. In some embodiments, the therapeutic compound may be mixed with monomers or polymers prior to gelation. In some embodiments, the therapeutic agent may be added to the hydrogel after the hydrogel has been formed. Where the therapeutic agent is loaded after formation, loading may involve exchanging or displacing a compound or fluid from the hydrogel and replacing the displaced fluid or compound with a therapeutic agent. Loading may also occur by absorption of the agent by the dried hydrogel. In some embodiments, the hydrogel may be loaded/unloaded by changing the environmental conditions (e.g., pH, temperature, solvent composition, ionic strength of solvent, etc.), Loading may be quantitated or described in terms of loading efficiency. Loading efficiency may be calculated by knowing the amount of therapeutic agent added to the hydrogel, and then measuring the amount of agent released during washing of the hydrogel—these values are then used to calculate the amount of therapeutic agent remaining.

The disclosed hydrogels may display high loading efficiency. In many embodiments, the loading efficiency is greater than about 40%, 45%, 50%, 55%, 60%, 65%, 70%, 75%, 80%, 85%, 90%, or 95% and less than about 100%, 95%, 90%, 85%, 80%, 75%, 70%, 65%, 60%, 55%, or 50%.

Release Rates

The disclosed hydrogels may be designed to release therapeutic compounds at a defined or prescribed rate. In some embodiments the release rate may be modified by varying one or more parameters of the hydrogel's manufacture. Variable aspects of the hydrogel that may affect release rates include the type, amount, or concentration of monomer contained within the gel, the type, amount, or concentration of cross linker, density of crosslinks, and pore size. Release rates describe the amount of therapeutic agent leaving the hydrogel as a function of time. Release rates may be determined by measuring the slope of a plot of the cumulative amount of therapeutic compound released from the hydrogel versus time. In some embodiments, the amount of therapeutic compound released at a given time is represented as a percentage of the total amount of therapeutic agent loaded.

Sustained/Steady Release

The rate of release of therapeutic agent from the disclosed hydrogel may vary over time. In most embodiments, an initial release rate is greater than a rate determined at a later time point. In some embodiments, release rate may be measured over days, weeks, or months, for example from about 2 days to about 200 days. A steady release rate is achieved when the slope of this plot (of % agent released versus time) is approximately constant (varying less than about 20%) and non-zero for more than about 7 days. A steady release rate may be between 0% and about 5% per day. In many embodiments, the steady release rate may be greater than about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.5%, or 4%, and less than about 5%, 4%, 3.5%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%. Preferably, the release rate is between about 0.2 and about 0.5%/day, and is maintained for between about one month and 5 months. A steady release rate over more than about 4 days may be referred to as a sustained release. Sustained release may be maintained for greater than about 7 days, 10 days, 20 days, 30 days, 2 months, 3 months, 4 months, 5 months, or more.

Burst Release

Where the disclosed hydrogel initially releases therapeutic agent at a greater rate, the initial release rate may be referred to as a burst release and the rate may vary significantly over this time. In some embodiments, a burst release may occur during days 0-7. In many embodiments, the disclosed hydrogel may display a burst release for less than about 7 days, 6 days, 5 days, 4 days, 3 days, 2 days, or 1 day. In most embodiments, the burst releases less than about 30% of the therapeutic agent, before achieving a steady release rate. In many embodiments the burst releases less than about 20%, 19%, 18%, 17%, 16%, 15%, 14%, 13%, 12%, 11%, 10%, 9%, 8%, 7%, 6%, or 5% of the therapeutic agent. In some embodiments, burst release from the disclosed hydrogels is less than about 10% after one day. For the applications disclosed herein, a desirable hydrogel is one which reaches and maintains a steady release rate for an extended time period with little to no burst release (also termed burst-free release rate).

EXAMPLES

A detailed description of the disclosed cryogels compositions and of methods to formulate these gels may be found in the experiments described below. The experiments described in this section analyze the engineering of hydrogels for providing the sustained release of a therapeutic agent. The following examples illustrate various aspects of the disclosure and are not meant to limit its scope or constrain the present invention to any particular agent, application, mechanism, mode, or theory of operation. It will be apparent to those skilled in the art that many modifications, both to materials and methods, may be made without departing from the scope of the disclosure.

Gel Preparation

Zwitterionic gels were prepared using [2-(methacryloyloxy)ethyl]dimethyl-(3-sulfopropyl) ammonium hydroxide (SBMA) as the zwitterionic monomers. For control experiments, non-ionic gels were prepared using 2-hydroxyethyl methacrylate (HEMA), which is a common non-ionic monomer for cryogel preparation, rather than SBMA. These gels are termed poly(SBMA) and poly(HEMA), respectively. The crosslinker was chosen to be glycerol dimethacrylate (GDMA), methylene bisacrylamide (MBA), or polyethylene glycol (PEG) diacrylates having different PEG chain lengths of Mn (number average molecular mass)=250 and Mn=700. Bovine serum albumin (BSA) and myoglobin were used as model proteins to investigate the protein loading efficiency. BSA was used as a model protein to investigate the protein release rate.

In a typical synthesis, predetermined amounts of monomer, crosslinker, and optionally protein for the protein-loaded gels, were mixed in millipore water and appropriate amounts of ammonium persulfate (APS) and N,N,N',N'-tetramethylethylene diamine (TEMED) were added to initiate the polymerization. The concentrations of the reagents for some representative BSA-loaded gels are provided in Table 1. The total volume of each gel was 0.5 mL. Polymerization was initiated using 50 μL of APS solution (13.6 mg/mL in water) and 0.85 μL of TEMED. The reaction mixtures were poured into plastic syringes (3 mL, inner diameter 0.5 cm) and polymerized at room temperature (RTgels) or −20° C. (cryogels) for 24 hours. The cryogels were thawed at room temperature. To remove unreacted monomers and other ingredients, the gel was washed three times with phosphate buffered saline (PBS) (5 mL) for at least 2 hours each for the first and second washings, and overnight for the third washing.

TABLE 1

Synthesis conditions of different poly(SBMA) and poly(HEMA) gels.

| Sample | SBMA (mg/mL) | HEMA (mg/mL) | GDMA (mg/mL) | MBA (mg/mL) | PEG (mg/mL) | BSA (mg/mL) | Polymerization conditions |
|---|---|---|---|---|---|---|---|
| poly(SBMA) cryogel 1 | 100 | — | 14 | — | | 20 | −20° C., 24 h |
| poly(SBMA) cryogel 2 | 100 | — | — | 9.4 | | 20 | −20° C., 24 h |
| poly(SBMA) cryogel 3 | 100 | | | | 40[a] | 20 | −20° C., 24 h |
| poly(SBMA) cryogel 4 | 100 | | | | 128[b] | 20 | −20° C., 24 h |
| poly(SBMA) RTgel 1 | 100 | — | 14 | — | | 20 | RT, 24 h |
| poly(HEMA) cryogel | — | 47 | — | — | | 20 | −20° C., 24 h |

TABLE 1-continued

Synthesis conditions of different poly(SBMA) and poly(HEMA) gels.

| Sample | SBMA (mg/mL) | HEMA (mg/mL) | GDMA (mg/mL) | MBA (mg/mL) | PEG (mg/mL) | BSA (mg/mL) | Polymerization conditions |
|---|---|---|---|---|---|---|---|
| poly(HEMA) RTgel | — | 47 | — | — | | 20 | RT, 24 h |

[a]polyethylene glycol (PEG) diacrylates having a PEG chain length of Mn = 250
[b]polyethylene glycol (PEG) diacrylates having a PEG chain length of Mn = 700

Gel Characterization

The morphology of a cross section of the dried samples were visualized by scanning electron microscopy (SEM). The hydrogels were freeze-dried prior to imaging to protect the pore structures. After gold sputter coating, SEM images of the hydrogels were taken on a FEI Quanta 600i Environmental SEM under high vacuum conditions.

Figure 1:
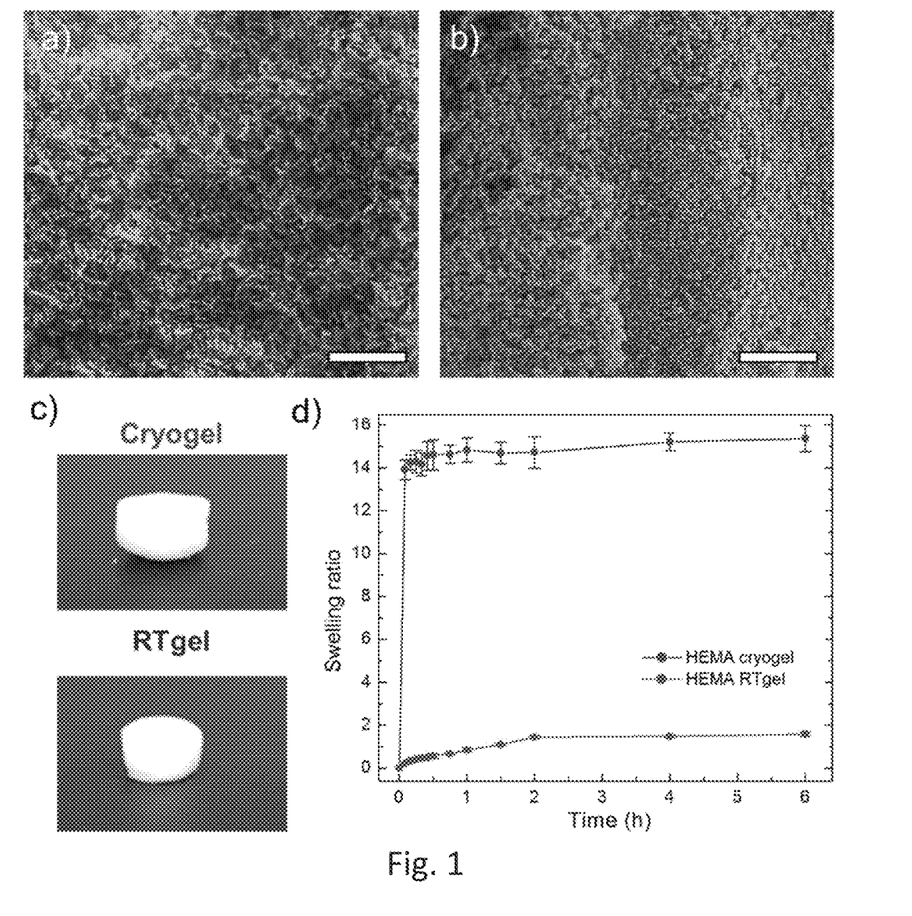
FIG. 1: Characterization of the poly(SMBA) hydrogels. SEM images of poly(SMBA) cryogels, panel (a), and in panel (b), poly(SMBA) RTgels. Scale bars are 250 µm. Panel (c) shows photographs of poly(SMBA) cryogels and poly(SMBA) RTgels. Panel (d) is a graph of the swelling of the dried poly(SMBA) cryogels and poly(SMBA) RTgels.
Figure 2:
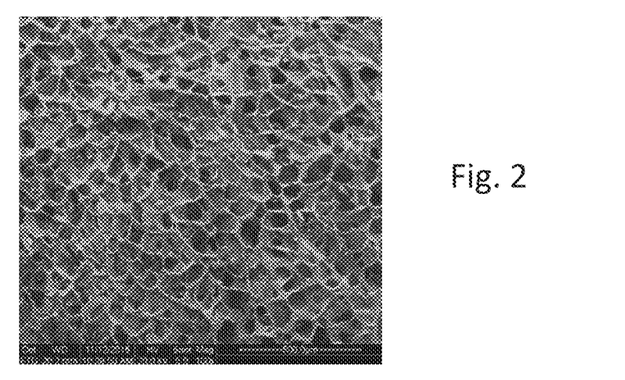
FIG. 2: SEM image of BSA-loaded (20 mg/mL) poly(SMBA) cryogel. Scale bar is 500 µm.

FIGS. 1a and b shows the SEM results for the poly (SBMA) zwitterionic cyrogel and RTgel (without protein loaded). The zwitterionic cryogel demonstrates a highly porous morphology. In contrast, the zwitterionic RTgel has a less porous polymer network with smaller and irregular pores. Photographs of the poly(SBMA) cyrogels and RTgels also highlight their differences (FIG. 1c); while the RTgel is slightly translucent, the cryogel is opaque. The difference in the appearance of the gels can be explained by the difference in their pore size. The larger pores of the cryogel scatters the light significantly and results in an opaque appearance, while the smaller pores of the RTgel can scatter the light less effectively and its appearance is translucent. The effect of BSA loading on the pore structure of poly(SBMA) cryogels was also explored. Even at the relatively high BSA concentration of 20 mg/mL, the morphology of poly(SBMA) cryogels was not significantly affected (FIG. 2).

Figure 3:
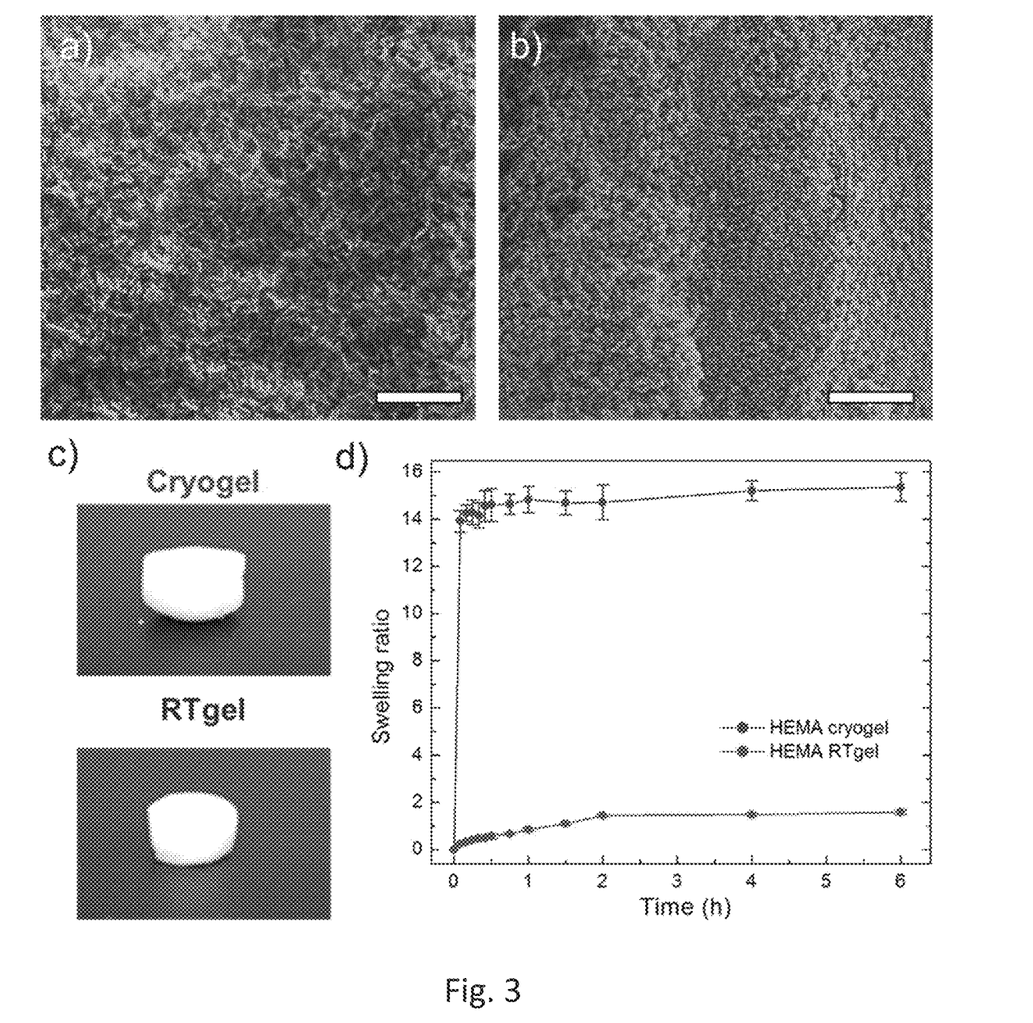
FIG. 3: Characterization of the poly(HEMA) hydrogels. SEM images of poly(HEMA) cryogels, panel (a), and poly(HEMA) RTgels, panel (b). Scale bars are 250 µm. Panel (c) contains photographs of poly(HEMA) cryogels and poly(HEMA) RTgels. Panel (d) is a graph showing swelling of the dried poly(HEMA) cryogels and poly(HEMA) RTgels.

A similar morphological difference was observed between the non-ionic poly(HEMA) cryogels and RTgels (FIGS. 3a and b); however, the pores of the poly(HEMA) hydrogels were smaller than their poly(SBMA) counterparts. The poly(HEMA) RTgels demonstrated a more porous structure than poly(SBMA) RTgels. Photographs of the poly(HEMA) hydrogels are also shown in FIG. 3c, both of poly(HEMA) hydrogels are opaque in appearance.

Swelling Tests

To determine the swelling behavior of the hydrogels, wet hydrogels were dried in an incubator at 37° C., and then weighed to determine the mass of dried samples (mdry gel). Then, they were soaked in distilled water and allowed to swell. The hydrogels were taken at selected time intervals. A kimwipe was used to remove the excess water from the hydrogel surface, and then they were weighed (mwet gel). The swelling ratio of the hydrogel was calculated according to the following equation: Swelling ratio=(mwet gel-mdry gel)/mdry gel.

Cryogels are known for their three-dimensional interconnected macroporous structure, which is formed by ice crystals during freezing and polymerization. When placed in aqueous solution, dried cryogels swell rapidly as a result of their interconnected porous structure. It was found that dried poly(SBMA) cryogels recover their initial shape and swell to around 11.5-fold of the dried mass in less than five minutes (FIG. 1d). In contrast, the RTgel could not fully recover its initial shape even after six hours of incubation in water. Similar results were also obtained with poly(HEMA) cryogels and RTgels (FIG. 3d).

Protein Loading

The loading efficiency of different RTgels and cryogels was determined by measuring the amount of protein released in the PBS washing solutions following the hydrogel preparation. Each gel was washed three times using 5 mL of PBS solution for at least 2 hours each for the first and second washings, and overnight for the third washing. The amount of protein released into the washing solution (Creleased) was measured by a UV-Vis spectrophotometer at 280 nm using an absorbance versus concertation calibration curve. The loading efficiency was determined by: Loading Efficiency=100×(Ctotal−Creleased)/Ctotal, where Ctotal is the total amount of protein used during hydrogel preparation.

Figure 4:
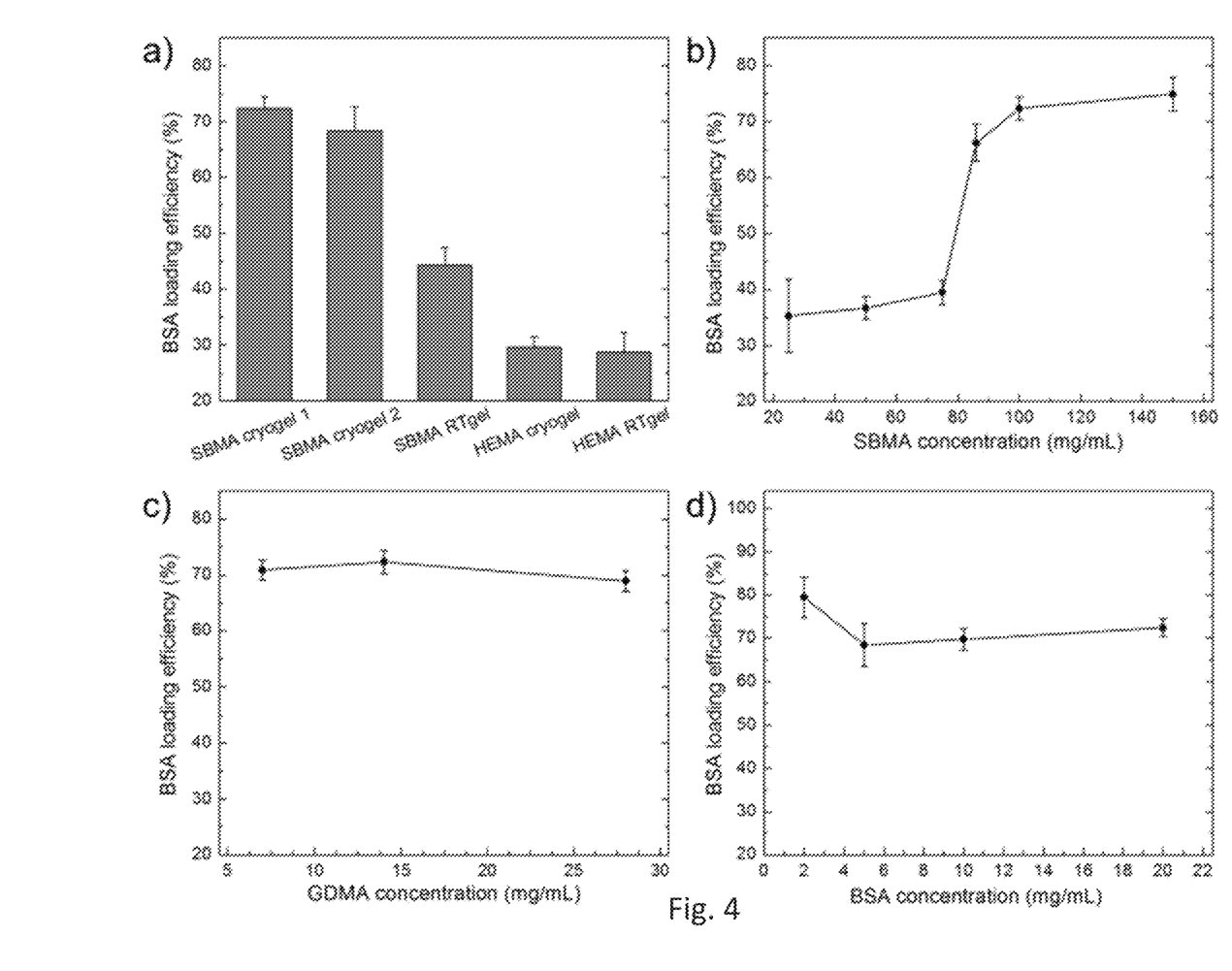
FIG. 4: BSA loading efficiency in the hydrogels. Panel (a) is a bar graph showing BSA loading efficiency for different poly(SBMA) and poly(HEMA) hydrogels; SBMA cryogel 1 and cryogel 2 are GDMA and MBA crosslinked cryogels, respectively. All other hydrogels were crosslinked with GDMA. Panel (b) is a graph that shows the effect of SBMA monomer concentration on the BSA loading efficiency in the poly(SBMA) cryogels. Panel (c) is a graph showing the effect of crosslinker (GDMA) concentration on the BSA loading efficiency in the poly(SBMA) cryogels. Panel (d) is a graph showing the effect of BSA concentration in the gelation solution on the BSA loading efficiency in the poly(SBMA) cryogels.

The loading efficiency for a variety of hydrogels are presented in FIG. 4. The BSA loading efficiency of the poly(SBMA) cryogels was around 70%, which is significantly higher than the loading efficiencies found for the poly(SBMA) RTgel. The loading efficiency for both poly (HEMA) RTgel and cryogel are comparable to each other and are lower than the poly(SMBA) gels. Next, the effect of monomer amount on the protein loading efficiency was investigated. It was observed that between 80 and 100 mg/mL of SBMA concentration, the loading efficiency sharply increased from 38% to 72% (FIG. 4b). Further increasing the SBMA concentration to 150 mg/mL in the gels solution did not significantly improve the loading efficiency. Thus, 100 mg/mL of SBMA concentration was determined to be an optimum monomer concentration for high protein loading and used in the rest of the study. The effect of the crosslinker amount on the protein loading efficiency of the poly(SBMA) cryogels was also investigated, and it was observed that changing the amount of crosslinker had no significant effect on protein loading (FIG. 4c). Finally, the BSA concentration in the gelation solution was varied between 2-20 mg/mL to determine its effect on encapsulation efficiency (FIG. 4d). BSA loading efficiency was almost independent from its concentration in the starting gelation solution, yet it was slightly higher (reaching 80%) at the lowest concentration used in this study (2 mg/mL).

Figure 5:
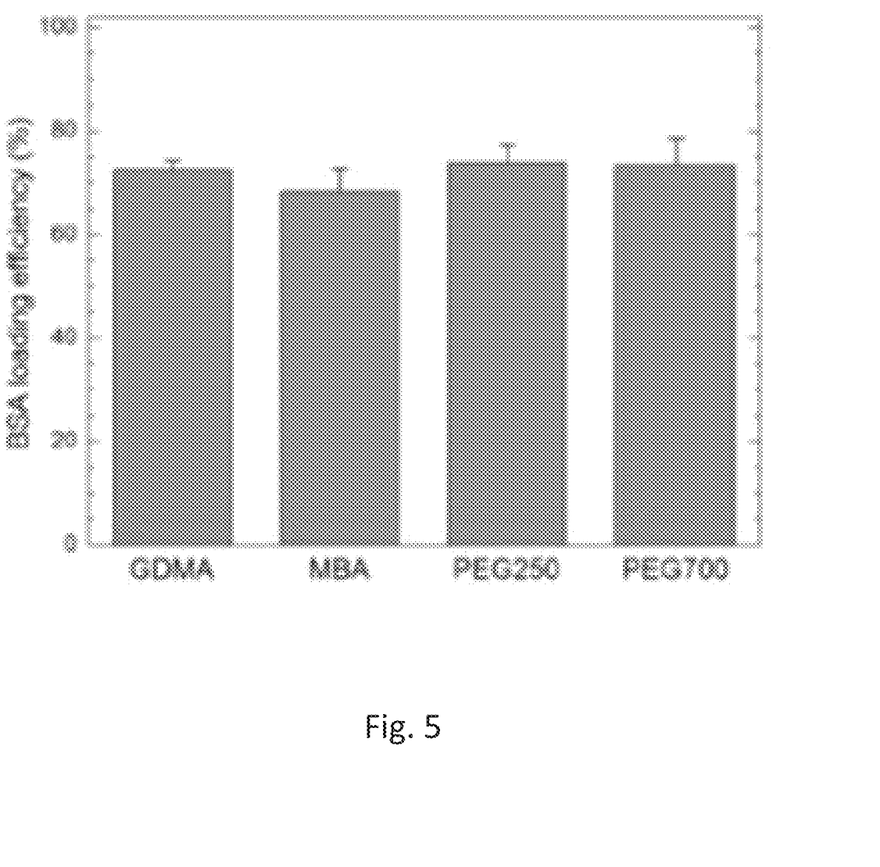
FIG. 5: Is a bar graph showing BSA loading efficiencies of zwitterionic cryogels prepared using different crosslinkers.

To investigate the impact of different crosslinkers on the protein loading and release, methylene bisacrylamide (MBA) and polyethylene glycol (PEG) crosslinked zwitterionic cryogels were also prepared. Two PEG crosslinked hydrogels were prepared using PEG diacrylates with different PEG chain lengths (Mn=250 and Mn=700). FIG. 5 shows the BSA loading efficiency to zwitterionic cryogels, which were prepared using the different crosslinkers. All four cryogels demonstrate high loading efficiency of about 70%. The loading efficiencies of the PEG crosslinked zwitterionic cryogels were slightly higher than the GDMA crosslinked cryogel, while the loading efficiency of the MBA cryogel is slightly less.

To investigate the effect of the protein charge on the loading efficiency, a neutral protein, myoglobin, with an isoelectronic point (pI) of 6.8 was loaded. (BSA is an acidic protein with a pI of 4.9.) The myoglobin-loaded poly(SBMA) cryogels were prepared using 100 mg/mL of SBMA, 14 mg/mL GDMA, and 5.2 mg/mL myoglobin to give the same molar ratio of protein as the BSA-loaded gels. A slightly better loading efficiency of 79% was observed for myoglobin-loaded poly(SBMA) cryogels; this indicates that the loading efficiency of acidic and neutral proteins is similar. It should also be noted that similar synthetic methods for the fabrication of protein-laden biomaterial systems crosslinked with radical chemistry have not demonstrated any significant change in the structure and function of proteins.

Protein Release Experiments

The protein release profiles from the gels was evaluated using BSA as a model protein. After optimizing the loading conditions, BSA release profiles were measured for poly(SBMA) cryogels, poly(SBMA) RTgels, poly(HEMA) cryogels, and poly(HEMA) RTgels, all with GDMA crosslinker. The BSA-loaded gels were placed into a 20 mL glass bottle filled with 5 mL of PBS (pH 7.4) or 2-morpholinoethane-sulfonic acid (MES) buffered saline (pH 5.5) and incubated at 37° C. At predetermined time points, release solutions were collected and replaced with 5 mL of fresh saline solution. To determine the released BSA amounts, absorption at 280 nm was measured by using an UV-Vis spectrophotometer and released amounts were calculated using an absorbance versus concertation calibration curve.

Figure 6:
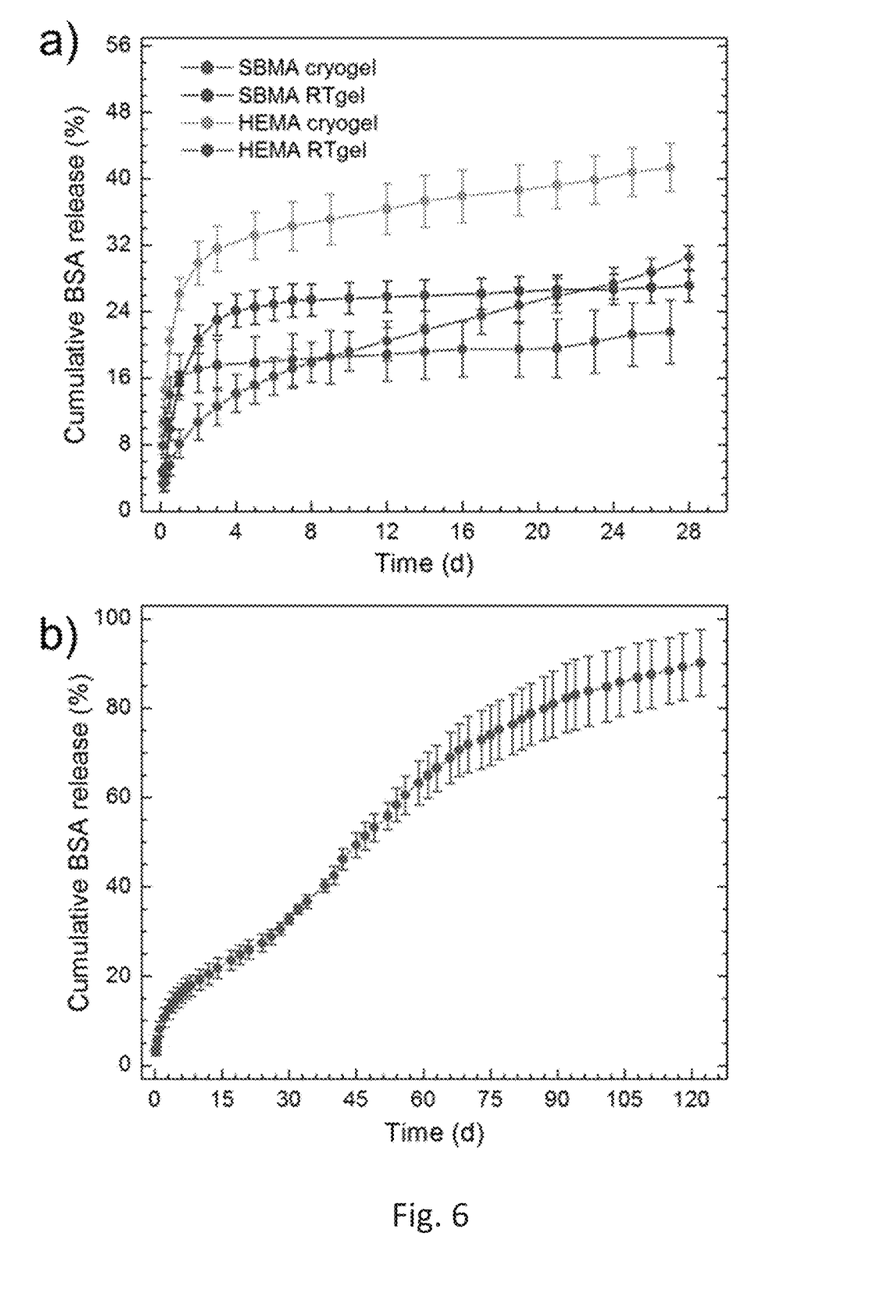
FIG. 6: A graph showing BSA release profiles of hydrogels. Panel (a) is a graph of BSA release from poly(SBMA) and poly(HEMA) cryogels and RTgels for 4 weeks. Panel (b) shows BSA release from poly(SBMA) cryogels showing sustained release for 4 months.
Figure 7:
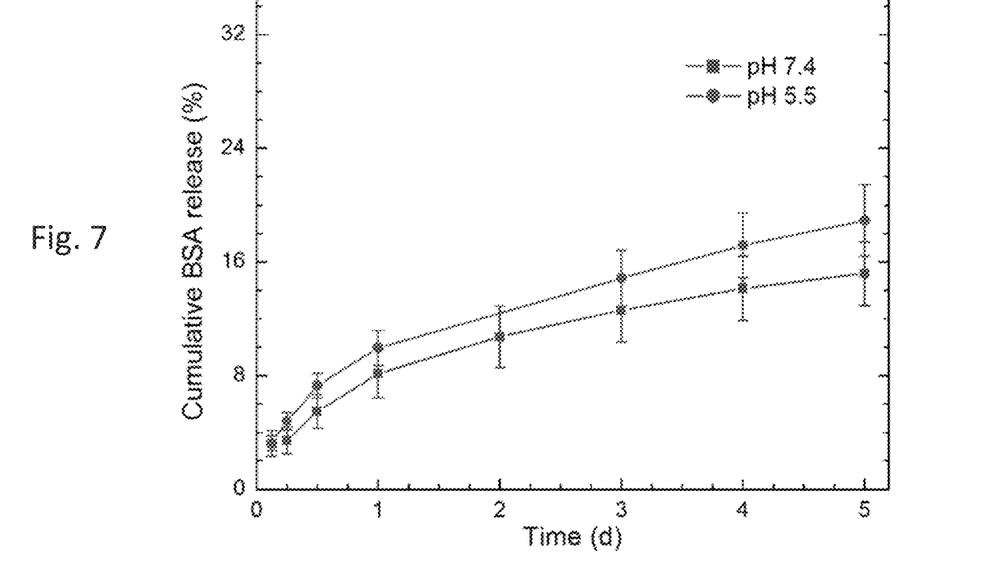
FIG. 7: A graph of BSA release from poly(SBMA) cryogels at acidic (pH 5.5) and neutral (pH 7.4) conditions. The gels were prepared using 100 mg/mL SBMA, 14 mg/mL GDMA and 20 mg/mL BSA.

FIG. 6 shows the BSA release from the hydrogels over the course of 4 weeks. Notably, for poly(SBMA) cryogels, the burst release was significantly low (only an average of 8% after one day), and the cumulative release linearly increased in the next three weeks and reached around 30%. The BSA release from poly(SBMA) cryogel continued for 4 months with almost a constant rate (FIG. 6b). For the poly(SBMA) RTgels, on the other hand, the initial BSA release was faster (cumulative release was an average of 16% after 1 day), and then it reached 24% at the end of the first week and remained almost constant up to 4 weeks. Similarly, poly(HEMA) hydrogels demonstrated high burst release, with averages of 26% and 17% after 1 day for cryogels and RTgels, respectively. Note that, since release was very slow, except for poly(SBMA) cryogel, measurements were stopped after 4 weeks for these hydrogels (FIG. 6a). The effect of pH on BSA release from poly(SBMA) cryogels is shown in FIG. 7. It was observed that in slightly acidic conditions (pH 5.5) the release rate of BSA was unchanged compared to its release at neutral pH.

Figure 8:
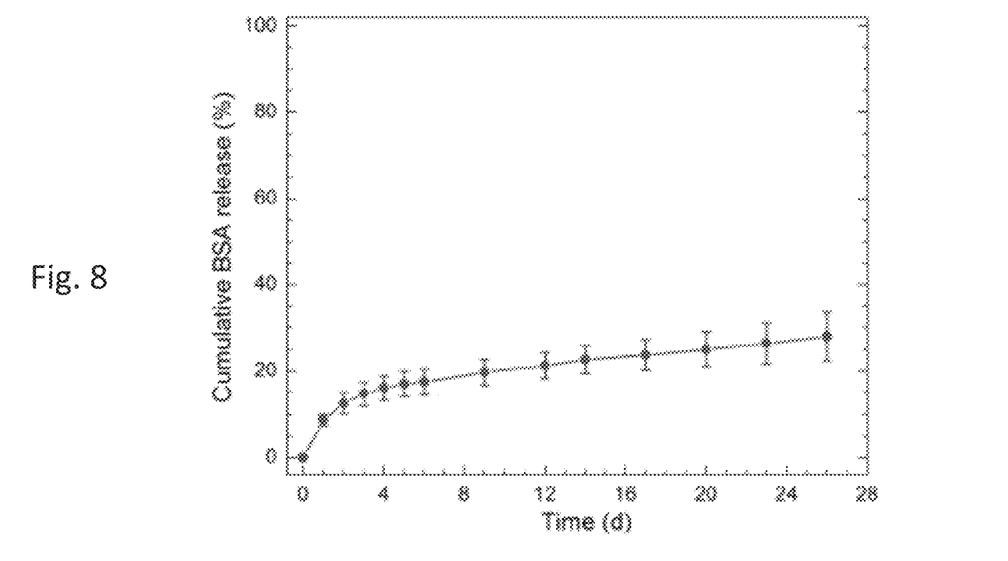
FIG. 8: As graph showing cumulative BSA release from PEG250 diacrylate crosslinked poly(SBMA) cryogel.

FIG. 8 shows the cumulative BSA release from the PEG250 diacrylate crosslinked poly(SBMA) zwitterionic cryogel. The release profile was very similar to the release profile of the GDMA crosslinked zwitterionic cryogel. It demonstrated a sustained release profile with a small burst release.

CONCLUSION

In summary, we report the preparation of hydrogels that show the potential for sustained protein release applications. The results from the swelling tests, along with the SEM observations, indicated that the zwitterionic cryogels display an interconnected macroporous structure. The zwitterionic cryogels demonstrated very high protein encapsulation efficiency (~70-80%) and sustained protein release profile over months with very little burst release. Interestingly, when the same materials were used to prepare hydrogels at room temperature, significantly lower protein encapsulation efficiency and a burst protein release was observed. In addition, non-ionic poly(HEMA) cryogels and RTgels demonstrated low protein loading efficiencies and burst protein release. With their interconnected macroporous structures and remarkable protein loading and release properties, the zwitterionic cryogels may prove useful for controlled macromolecular therapeutic delivery and tissue engineering applications.

Although this present disclosure has been described with a certain degree of particularity, it is understood the disclosure has been made by way of example, and changes in the detail or structure may be made without departing from the spirit of the disclosure as defined in the appended claims.

What is claimed is:

1. A method of making a cryogel, comprising the steps of:
   mixing a zwitterionic monomer of 2-(methylacryloyloxy) ethyl]dimethyl-(3-sulfoproplyl)ammonium hydroxide and a crosslinking agent selected from glycerol dimethyacrylate, N,N'-methylbis(acrylamide), and polyethylene glycol, with one or more initiator compounds in an aqueous solution;
   cooling the aqueous solution to at least −20° C. while the monomers are crosslinked to form the cryogel;
   thawing the cryogel to room temperature; and
   washing the cryogel to remove unreacted monomers, crosslinking agents, and initiator compounds, wherein the cryogel has an average pore size that is greater than about 50 μm and less than about 100 μm.

2. The method of claim 1, wherein a therapeutic agent is added to the aqueous solution prior to cooling.

3. The method of claim 1, wherein the crosslinking agent is selected from glycerol dimethyacrylate, and polyethylene glycol.

4. The method of claim 1, further comprising the step of adding a therapeutic agent to the washed cryogel.

5. The method of claim 2, wherein the therapeutic agent is a protein.

6. The method of claim 3, wherein the crosslinking agent is glycerol dimethyacrylate.

7. The method of claim 1, wherein the crosslinking agent is N,N'-methylbis(acrylamide).

8. The method of claim 3, wherein the crosslinking agent is polyethylene glycol.

9. The method of claim 1, further comprising the step of drying the cryogel.

10. The method of claim 9, further comprising the step of rehydrating the dried cryogel.

11. The method of claim 6, wherein a therapeutic agent is added to the aqueous solution prior to cooling.

12. The method of claim 6, further comprising the step of adding a therapeutic agent to the washed cryogel.

13. The method of claim 12, wherein the therapeutic agent is a protein.

14. The method of claim 7, wherein a therapeutic agent is added to the aqueous solution prior to cooling.

15. The method of claim 7, further comprising the step of adding a therapeutic agent to the washed cryogel.

16. The method of claim 15, wherein the therapeutic agent is a protein.

17. The method of claim 16, wherein a therapeutic agent is added to the aqueous solution prior to cooling.

18. The method of claim 16, further comprising the step of adding a therapeutic agent to the washed cryogel.

19. The method of claim 18, wherein the therapeutic agent is a protein.

* * * * *